(12) United States Patent
Akasaka et al.

(10) Patent No.: US 11,753,354 B2
(45) Date of Patent: Sep. 12, 2023

(54) PRODUCTION SYSTEM AND PRODUCTION METHOD FOR METHANE

(71) Applicant: ROHM Co., LTD., Kyoto (JP)

(72) Inventors: Shunsuke Akasaka, Kyoto (JP); Yoshiaki Oku, Kyoto (JP)

(73) Assignee: ROHM CO., LTD., Kyoto (JP)

( * ) Notice: Subject to any disclaimer, the term of this patent is extended or adjusted under 35 U.S.C. 154(b) by 0 days.

(21) Appl. No.: 17/498,902

(22) Filed: Oct. 12, 2021

(65) Prior Publication Data
US 2022/0112139 A1 Apr. 14, 2022

(30) Foreign Application Priority Data
Oct. 13, 2020 (JP) .................... 2020-172584

(51) Int. Cl.
*C07C 1/12* (2006.01)
*C25B 15/08* (2006.01)
*C25B 1/04* (2021.01)
*H10N 10/10* (2023.01)

(52) U.S. Cl.
CPC ............ *C07C 1/12* (2013.01); *C25B 1/04* (2013.01); *C25B 15/081* (2021.01); *H10N 10/10* (2023.02)

(58) Field of Classification Search
CPC ........... C07C 1/12; C25B 1/04; C25B 15/081; Y02E 60/36
See application file for complete search history.

(56) References Cited

U.S. PATENT DOCUMENTS 3,070,645 A * 12/1962 Tracht ................... H01L 35/30
374/E7.004
2017/0167038 A1* 6/2017 Hashiba ................ C25B 11/044

FOREIGN PATENT DOCUMENTS

JP 2009119502 6/2009

OTHER PUBLICATIONS

De Lucas-Consuegra et al., Coupling catalysis and electrocatalysis for hydrogen production in a solid electrolyte membrane reactor, (Applied Catalysis A: General vol. 483, Aug. 5, 2014, pp. 25-30).*
Kamata Hiroyuki, "Catalyst for CO2 Conversion to Fuel and Useful Chemicals" (in Japanese), IHI Technical Reports, vol. 59, No. 1, Mar. 2019).

* cited by examiner

*Primary Examiner* — Jafar F Parsa
(74) *Attorney, Agent, or Firm* — CHIP LAW GROUP

(57) ABSTRACT

Disclosed is a production system for methane, including a reaction vessel having a solid electrolyte membrane and an electrode group including at least a pair of electrodes arranged on the solid electrolyte membrane, in which one of the electrodes functions as a cathode side electrode, and the other electrode functions as an anode side electrode, and the one electrode that functions as the cathode side electrode includes a hydrogenation catalyst.

5 Claims, 5 Drawing Sheets

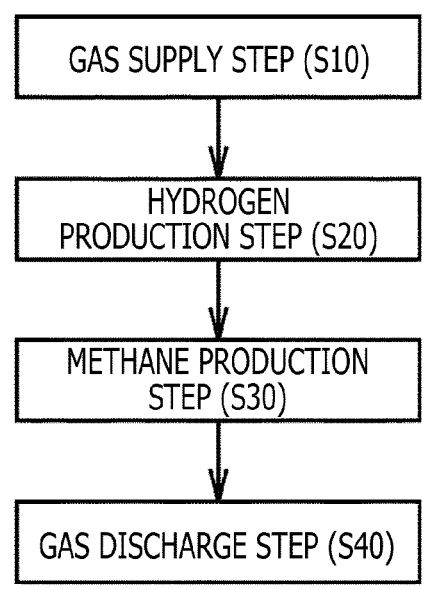

PRODUCTION SYSTEM AND PRODUCTION METHOD FOR METHANE

CROSS REFERENCE TO RELATED APPLICATIONS

This application claims priority benefit of Japanese Patent Application No. JP 2020-172584 filed in the Japan Patent Office on Oct. 13, 2020. Each of the above-referenced applications is hereby incorporated herein by reference in its entirety.

BACKGROUND

The present disclosure relates to a production system and a production method for methane.

A method that performs electrolysis of water with use of recyclable energy and reacts the resulting hydrogen with carbon dioxide to produce methane is known in the past (see KAMATA Hiroyuki, "Catalyst for $CO_2$ Conversion to Fuel and Useful Chemicals" (in Japanese), IHI Technical Reports, Vol. 59, No. 1, March 2019).

SUMMARY

In many of production methods for methane in the past, two kinds of apparatuses may be necessary; one for producing hydrogen by electrolysis of water, and the other for producing methane through a reaction between the hydrogen and carbon dioxide, or two steps are separately performed; one for producing hydrogen by the electrolysis of water, and the other for producing methane through the reaction between the hydrogen and carbon dioxide. Such production methods for methane in the past may thus be unable to perform efficient production of methane.

It is desirable to provide a production system and a production method for methane that can concurrently perform production of hydrogen by electrolysis of water and production of methane through a reaction of the hydrogen with carbon dioxide, without needing a plurality of apparatuses.

It is also desirable to provide a production system and a production method for methane that, using recyclable energy, can concurrently perform production of hydrogen by electrolysis of water and production of methane through a reaction of the hydrogen with carbon dioxide, without needing a plurality of apparatuses.

It is further desirable to provide a production system and a production method for methane that, using $CO_2$-containing exhaust gas from an internal combustion engine, can concurrently perform production of hydrogen by electrolysis of water and production of methane through a reaction of the hydrogen with carbon dioxide, without needing a plurality of apparatuses.

The present disclosure provides the following production systems and production methods for methane:

[1] A production system for methane, including:
a reaction vessel having a solid electrolyte membrane and an electrode group that includes at least a pair of electrodes arranged on the solid electrolyte membrane,
in which one of the electrodes functions as a cathode side electrode, and the other electrode functions as an anode side electrode, and
the one electrode that functions as the cathode side electrode includes a hydrogenation catalyst.

[2] The production system for methane as described above in [1], in which the hydrogenation catalyst is platinum.

[3] The production system for methane as described above in [1] or [2], in which the solid electrolyte membrane includes yttria-stabilized zirconia.

[4] The production system for methane as described above in any one of [1] to [3], further including:
an internal combustion engine.

[5] The production system for methane as described above in any one of [1] to [4], further including:
a thermoelectric generator.

A production method for methane, including:
a gas supply step of supplying gas that contains carbon dioxide and water into a reaction vessel;
a hydrogen production step of producing hydrogen by subjecting water to electrolysis in the reaction vessel with use of a solid electrolyte membrane having an electrode group including at least a pair of electrodes, one of the electrodes functioning as a cathode side electrode, the other electrode functioning as an anode side electrode, the one electrode that functions as the cathode side electrode including a hydrogenation catalyst;
a methane production step of producing methane by reacting hydrogen and carbon dioxide in presence of the hydrogenation catalyst in the reaction vessel; and
a gas discharge step of discharging gas that contains the methane, from the reaction vessel.

[7] The production method as described above in [6], in which, in the hydrogen production step, electrolysis is performed by electric power supplied from a thermoelectric generator.

[8] The production method as described above in [6] or [7], in which the hydrogen production step and the methane production step are performed concurrently.

According to an embodiment of the present disclosure, there are provided a production system and a production method for methane that can concurrently perform production of hydrogen by electrolysis of water and production of methane through a reaction of the hydrogen with carbon dioxide, without needing a plurality of apparatuses.

There are also provided a production system and a production method for methane that, using recyclable energy, can concurrently perform production of hydrogen by electrolysis of water and production of methane through a reaction of the hydrogen with carbon dioxide, without needing a plurality of apparatuses.

There are also provided a production system and a production method for methane that, using $CO_2$-containing exhaust gas from an internal combustion engine, can concurrently perform production of hydrogen by electrolysis of water and production of methane through a reaction of the hydrogen with carbon dioxide, without needing a plurality of apparatuses.

BRIEF DESCRIPTION OF THE DRAWINGS

FIG. 5 is a flow chart of a production method according to an embodiment of a second mode of the present disclosure for methane.

DETAILED DESCRIPTION OF THE PREFERRED EMBODIMENTS

First to fourth embodiments of a first mode and an embodiment of a second mode of the present disclosure will hereinafter be described with reference to the accompanying drawings, but the present disclosure should not be limited to or by the following embodiments. In all figures to be referred to below, individual elements are illustrated at scales appropriately adjusted to facilitate understanding, and the dimensional relations among the individual elements illustrated in the figures do not necessarily conform to those among actual elements.

Production System for Methane

Figure 1:
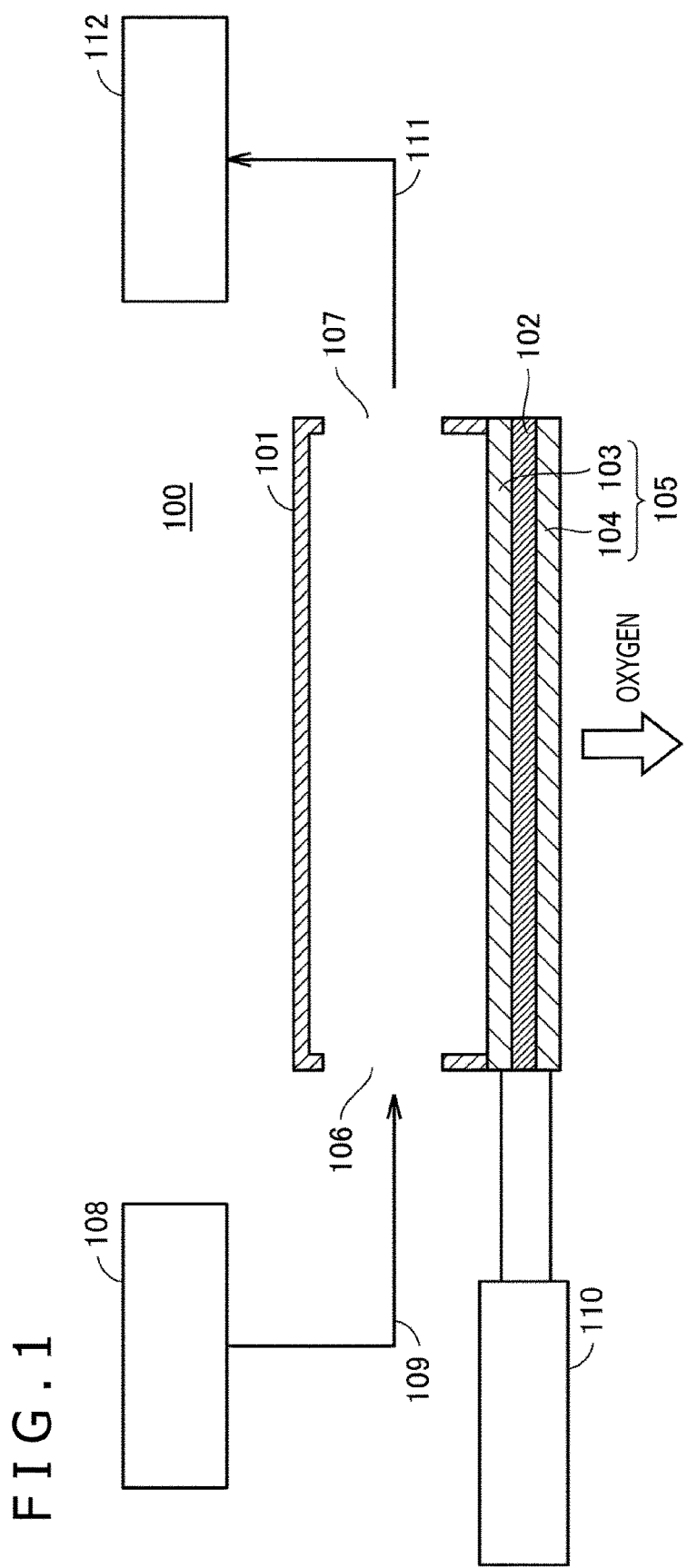
FIG. 1 is a schematic vertical cross-sectional view of a production system according to a first embodiment of a first mode of the present disclosure for methane.

Regarding a production system according to a first embodiment of a first mode of the present disclosure for methane (hereinafter called the "methane production system of the first embodiment"), a description will be made with reference to FIG. 1. FIG. 1 is a schematic vertical cross-sectional view of the methane production system of the first embodiment. A production system 100 for methane includes a reaction vessel 101, and the reaction vessel 101 has a solid electrolyte membrane 102 and an electrode group 105 that includes a pair of electrodes 103 and 104 arranged on the solid electrolyte membrane 102.

The reaction vessel 101 further has an inlet 106. Gas that contains carbon dioxide and water is supplied from the inlet 106 into the reaction vessel 101. This gas will be described in further detail subsequently herein.

In the reaction vessel 101, the gas that contains carbon dioxide and water comes into contact with the electrode group 105, whereby electrolysis of water takes place to produce hydrogen and oxygen. As will be described below, the hydrogen produced through the electrolysis and carbon dioxide react with each other in presence of a hydrogenation catalyst, so that methane and water are produced. The water so produced is subjected to electrolysis to produce hydrogen and oxygen.

The methane production system of the first embodiment can perform the electrolysis of water and the production of methane without using a plurality of apparatuses, and thus does not need to separately install apparatuses or facilities for performing the electrolysis of water and the production of methane and to install apparatuses or facilities for storing and transporting the produced hydrogen. The methane production system of the first embodiment is hence advantageous from the viewpoints of the cost incurred for such facilities and the installation space.

The reaction vessel 101 further has an outlet 107. Gas that contains the methane so produced is taken out from the outlet 107.

The reaction vessel 101 may include a heater to heat the gas in the reaction vessel 101 such that the reaction of carbon dioxide and hydrogen is facilitated.

The solid electrolyte membrane 102 can include at least one kind of solid electrolyte material. Examples of the solid electrolyte material include yttria-stabilized zirconia ($ZrO_2$—$Y_2O_3$; hereinafter abbreviated as "YSZ" in some cases), cerium oxide ($CeO_2$), lanthanum gallate ($LaGaO_3$), and other materials. As the solid electrolyte material, preferred is YSZ.

Inclusion of YSZ in the solid electrolyte membrane 102 is advantageous, because, owing to the occurrence of a difference in oxygen partial pressure between an inside and an outside of the reaction vessel 101 by the electrolysis, migration of oxygen ions takes place in the YSZ, resulting in facilitated promotion of the electrolysis. In addition, the inclusion of YSZ in the solid electrolyte membrane 102 is also advantageous from the viewpoint of safety, because the oxygen produced through the electrolysis is more easily discharged out of the reaction vessel 101 through the solid electrolyte membrane 102, thereby making the oxygen less prone to a reaction with hydrogen.

The solid electrolyte membrane 102 can be, for example, a printed membrane being formed on a substrate and including a solid electrolyte material. The substrate can be, for example, a silicon substrate (which may also be referred to as an "Si substrate" below). The substrate may have a thickness of, for example, 10 μm or smaller. If a microheater is formed on the substrate as will be described subsequently herein, the thickness of the substrate may be, preferably, 2 μm or smaller from the viewpoint of facilitating conduction of heat.

If the solid electrolyte membrane 102 includes YSZ, the microheater can make the YSZ easier to function. If the microheater is formed on the substrate, the microheater can be formed in a state of being sandwiched between insulating membranes. The microheater can be formed, for example, wavy in plan view of the substrate (as seen in a thickness direction of the substrate). Examples of the insulating membranes include printed $SiO_2$ membranes, printed $Al_2O_3$ membranes, and other membranes.

The solid electrolyte membrane 102 may be arranged so as to be exposed at one side thereof to the outside of the reaction vessel 101. The exposure of the one side of the solid electrolyte membrane 102 to the outside of the reaction vessel 101 can facilitate discharge of oxygen that is produced by the electrolysis of water to the outside of the reaction vessel 101.

The electrode group 105 includes at least a pair of electrodes. From the viewpoint of allowing the electrode group 105 to function as an anode and a cathode in the electrolysis of water, the electrode group 105 can be a pair of electrodes or a plurality of pairs of electrodes. Here, for the sake of convenience of description, the electrode group 105 is assumed to include a pair of electrodes. In FIG. 1, the electrode 103 can function as a cathode side electrode, while the electrode 104 can function as an anode side electrode. The paired electrodes that constitute the electrode group 105 may be formed as the electrodes 103 and 104 on opposite sides of the solid electrolyte membrane 102, respectively, as illustrated in FIG. 1, or the paired electrodes may both be formed on one side of the solid electrolyte membrane 102, the one side being located inside the reaction vessel 101. If the paired electrodes are both formed on the one side of the solid electrolyte membrane 102, the one side being located inside the reaction vessel 101, the paired electrodes may be formed, for example, as comb-shaped electrodes. As illustrated in FIG. 1, the arrangement of the electrode 104 as an anode side electrode on an outer wall of the reaction vessel 101 tends to facilitate the discharge of oxygen out of the reaction vessel 101.

Of the paired electrodes that constitute the electrode group 105, the electrode that functions as the cathode side electrode, i.e., the electrode 103, includes the hydrogenation catalyst. The inclusion of the hydrogenation catalyst in the electrode 103 facilitates contact of the hydrogen that is produced on the cathode side through the electrolysis of water and the carbon dioxide that is contained in the supplied gas, with the hydrogenation catalyst, so that methane can be produced efficiently. In addition, water that is produced along with the methane is also facilitated to come into contact with the electrodes shortly after its production, whereby electrolysis of water is also performed efficiently.

Examples of the hydrogenation catalyst include rhodium (Rh), palladium (Pa), platinum (Pt), nickel (Ni), and other metallic elements. As the hydrogenation catalyst, platinum is preferred from the viewpoint of the conversion rate of carbon dioxide into methane at an elevated temperature.

The electrodes 103 and 104 that constitute the electrode group 105 may both include the hydrogenation catalyst, or only the cathode side electrode 103 may include the hydrogenation catalyst. If the electrodes 103 and 104 that constitute the electrode group 105 both include the hydrogenation catalyst, the formation of both the electrodes 103 and 104 on the one side of the solid electrolyte membrane 102, the one side being located inside the reaction vessel 101, is advantageous in the reaction between hydrogen and carbon dioxide. Preferably, the electrode 103 includes the hydrogenation catalyst. If the electrode 104 also includes the hydrogenation catalyst, the electrode 104 also preferably includes the hydrogenation catalyst.

The electrodes 103 and 104 may be porous electrodes, with porous platinum electrodes being preferred. Use of the porous platinum electrodes as the electrodes 103 and 104 is advantageous from the viewpoint of the discharge of oxygen. The electrodes 103 and 104 can be, for example, printed electrodes formed by printing. The electrodes 103 and 104 are preferably printed porous electrodes, with printed porous platinum electrodes being more preferred.

The electrodes 103 and 104 may have a thickness of, for example, 50 nm or greater but 20 μm or smaller. If the electrodes 103 and 104 are printed electrodes, they may have a thickness of, for example, 100 nm or greater but 1,000 nm or smaller.

The solid electrolyte membrane 102 may have a porous membrane to cover the electrodes 103 and 104. Examples of the porous membrane include an $Al_2O_3$ membrane, $SiO_2$ membrane, MgO membrane, amorphous glass membrane, and other membranes. The porous membrane may have a thickness of, for example, 50 nm or greater but 20 μm or smaller. The porous membrane may be, for example, a printed membrane formed by printing.

The solid electrolyte membrane 102, the electrodes 103 and 104, the substrate, the microheater, the insulating membranes, and the porous membrane can be changed in shape and dimensions as needed depending on the desired production capacity of methane, the shape of the reaction vessel for methane, and the use of methane.

As a supply source 108 of the gas that contains carbon dioxide and water, an internal combustion engine may be further included, for example. Examples of the internal combustion engine include internal combustion engines or other engines used in a thermal power plant and an automotive vehicle. Exhaust gas from an internal combustion can be delivered into the reaction vessel 101, for example, through piping 109 connected to the inlet 106. In the piping 109, a valve and a flow rate meter may be arranged. Exhaust gas generally contains carbon dioxide and water, and is thus suitable as gas that contains carbon dioxide and water and is to be supplied to the methane production system of the first embodiment. The use of exhaust gas in the methane production system of the first embodiment is advantageous from the viewpoint of prevention of environmental contamination.

The temperature of the gas that contains carbon dioxide and water may be, but is not particularly limited to, for example, room temperature, or a temperature lower or higher than room temperature. Even if the temperature of the gas that contains carbon dioxide and water is relatively low, carbon dioxide and hydrogen can be facilitated to react with each other by heating of the solid electrolyte membrane 102.

As a supply source 110 of electric power to be supplied to the electrode group 105, for example, a thermoelectric generator, a regenerative energy generator, or other generators can be further included. If the supply source 110 is a thermoelectric generator, electric power can be generated by heat produced in an internal combustion engine. As this internal combustion engine, the internal combustion engine used as the above-mentioned supply source 108 can also be used in common. The heat produced from the internal combustion engine may have a temperature of, for example, 300° C. or higher but 650° C. or lower, preferably 400° C. or higher but 600° C. or lower.

Examples of a material for use in the thermoelectric generator include an antimony-tellurium based (Sb—Te based) material, a bismuth-tellurium based (Bi—Te based) material, a lead-tellurium based (Pb—Te based) material, a skutterudite antimony compound, a silicon-germanium based (Si—Ge based) material, and other materials. If the supply source 108 is an internal combustion engine, an antimony-tellurium based (Sb—Te based) material or a bismuth-tellurium based (Bi—Te based) material is preferred from the viewpoint of the temperature of heat produced from the internal combustion engine.

The regenerative energy generator may be, for example, regenerative brakes of an automotive vehicle, an electric train, or other vehicles. Electric power generated by the regenerative brakes can be stored in lithium-ion batteries or other batteries, which can then be used as a supply source 110 of electric power to be supplied to the electrode group 105.

The reaction vessel 101 can discharge a methane-containing gas, for example, from the outlet 107 via a piping 111. In the piping 111, a valve and a flow rate meter may be arranged. The discharged methane-containing gas can be supplied to a methane separator 112 or other devices connected, for example, to the outlet 107 by way of the piping 111. As the methane separator 112, the methane separator described in Japanese Patent Laid-open No. 2007-297605 can be used, for example.

The methane production system of the first embodiment can produce methane directly from recyclable energy, and can easily be downsized. The methane production system of the first embodiment can thus be installed, for example, in an automotive vehicle or a thermal power plant. A fuel cell vehicle or thermal power plant with the methane production system of the first embodiment installed therein can use the produced methane as fuel and its exhaust gas is clean, and is thus advantageous from the viewpoints of improvements in fuel economy and the prevention of environmental contamination.

Figure 2A:
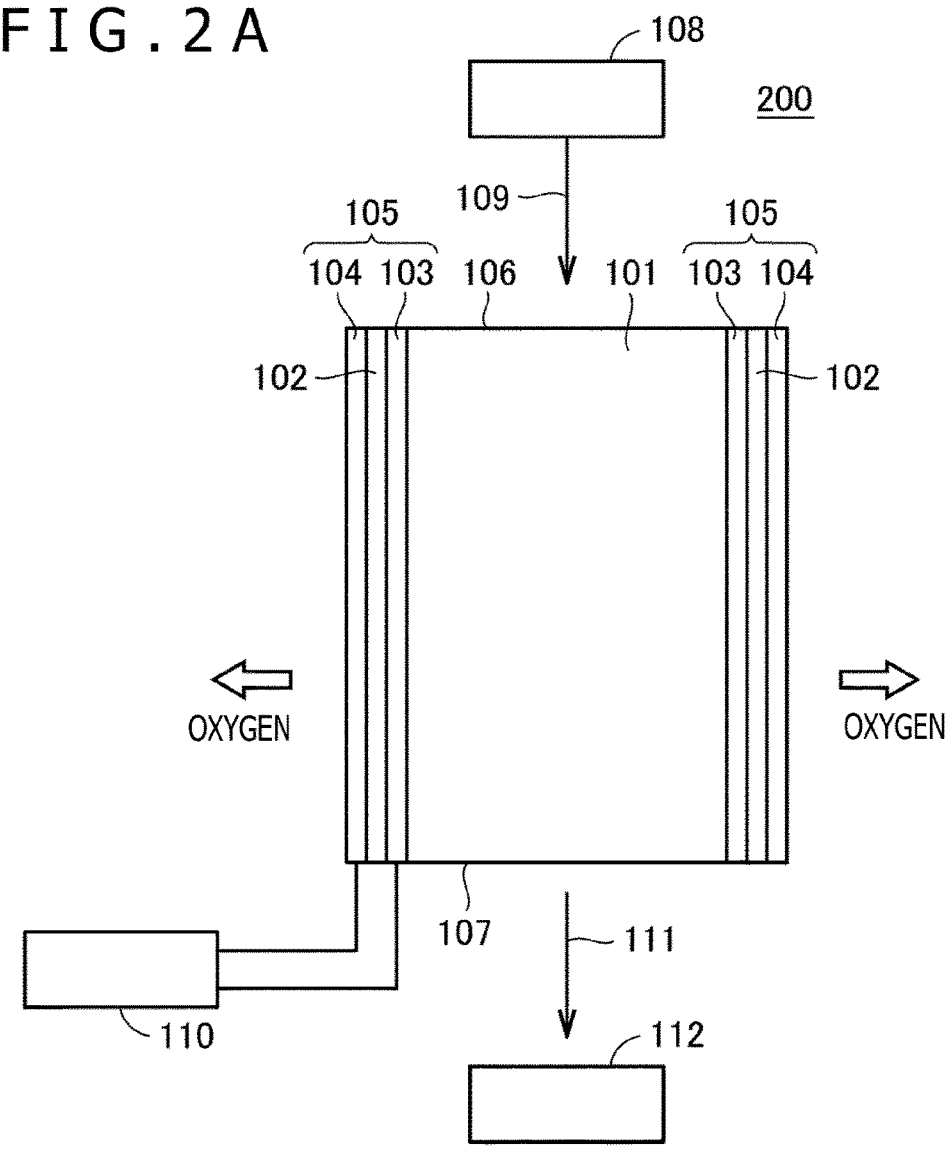
FIG. 2A is a schematic vertical cross-sectional view of a production system according to a second embodiment of the first mode of the present disclosure for methane.
Figure 2B:
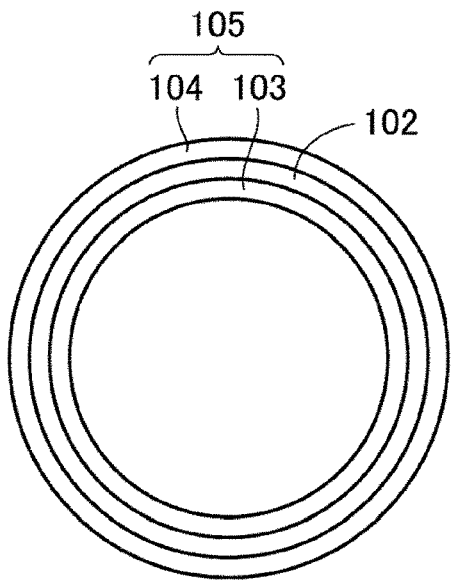
FIG. 2B is a schematic horizontal cross-sectional view of FIG. 2A.

FIGS. 2A and 2B illustrate a production system according to a second embodiment of the first mode of the present disclosure for methane (hereinafter called the "methane production system of the second embodiment"). FIG. 2A is a schematic vertical cross-sectional view of the methane production system of the second embodiment, and FIG. 2B is a schematic horizontal cross-sectional view of FIG. 2A. To elements illustrated in FIGS. 2A and 2B and designated by the same reference numerals as in FIG. 1, the above description is applicable. The methane production system of FIGS. 2A and 2B includes a cylindrical reaction vessel 101. The reaction vessel 101 has an outer wall formed by a cylindrical solid electrolyte membrane 102 that includes cylindrical electrodes 103 and 104. Gas that is supplied from an inlet 106 and contains carbon dioxide and water comes into contact with the electrode 103, whereby electrolysis of water and production of methane take place. A methane-containing gas is then taken out from an outlet 107. Oxygen produced through the electrolysis of water is discharged out of the cylindrical reaction vessel 101 through the cylindrical solid electrolyte membrane 102. Owing to their cylindrical shapes, gas is allowed to flow well and hardly undergoes stagnation, so that the production of methane can be performed efficiently.

Figure 3A:
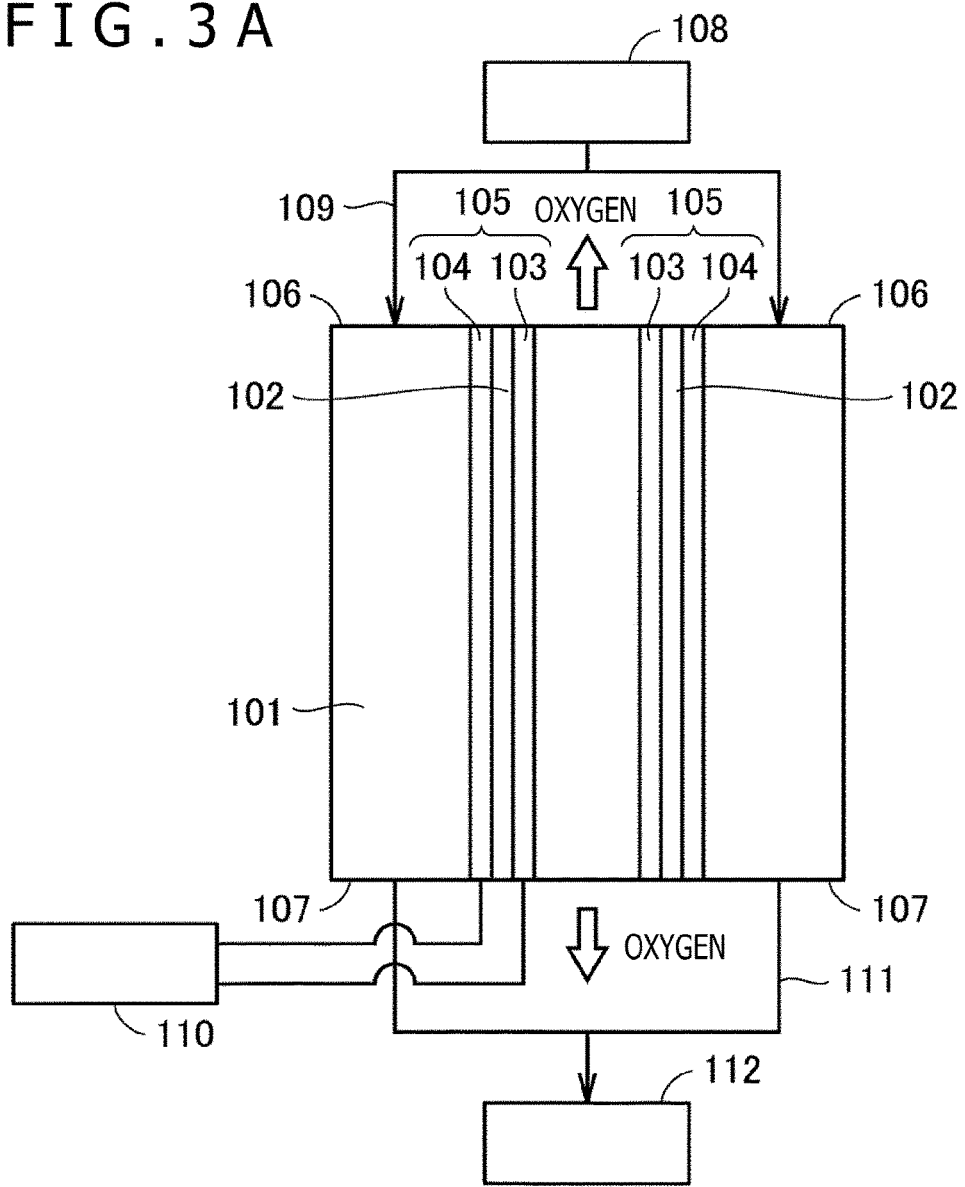
FIG. 3A is a schematic vertical cross-sectional view of a production system according to a third embodiment of the first mode of the present disclosure for methane.
Figure 3B:
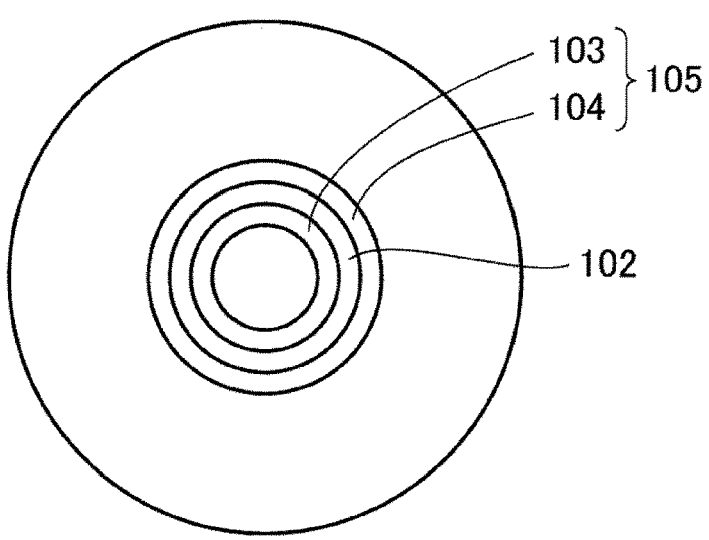
FIG. 3B is a schematic horizontal cross-sectional view of FIG. 3A.

FIGS. 3A and 3B illustrate a production system according to a third embodiment of the first mode of the present disclosure for methane (hereinafter called the "methane production system of the third embodiment"). FIG. 3A is a schematic vertical cross-sectional view of the methane production system of the third embodiment, and FIG. 3B is a schematic horizontal cross-sectional view of FIG. 3A. To elements illustrated in FIGS. 3A and 3B and designated by the same reference numerals as in FIG. 1, the above description is applicable. The methane production system of FIGS. 3A and 3B includes a cylindrical reaction vessel 101. A cylindrical solid electrolyte membrane 102 that includes cylindrical electrodes 103 and 104 on outer and inner surfaces thereof, respectively, is arranged in the cylindrical reaction vessel 101. The cylindrical solid electrolyte membrane 102 is thus sandwiched between the cylindrical electrode 103 and the cylindrical electrode 104. The cylindrical reaction vessel 101 and the cylindrical solid electrolyte membrane 102 are coaxially arranged. Gas that is supplied from an inlet 106 and contains carbon dioxide and water comes into contact with the electrode 103, whereby electrolysis of water and production of methane take place. A methane-containing gas is then taken out from an outlet 107. Oxygen produced through the electrolysis of water is discharged out of the cylindrical reaction vessel 101 through the cylindrical solid electrolyte membrane 102. Owing to their cylindrical shapes, the production of methane can be performed efficiently. With the methane production system of the third embodiment illustrated in FIGS. 3A and 3B, gas is allowed to flow well and hardly undergoes stagnation, so that the production of methane can be performed efficiently. Moreover, the produced oxygen can be collected, and can then be delivered to a specific discharge destination.

Figure 4A:
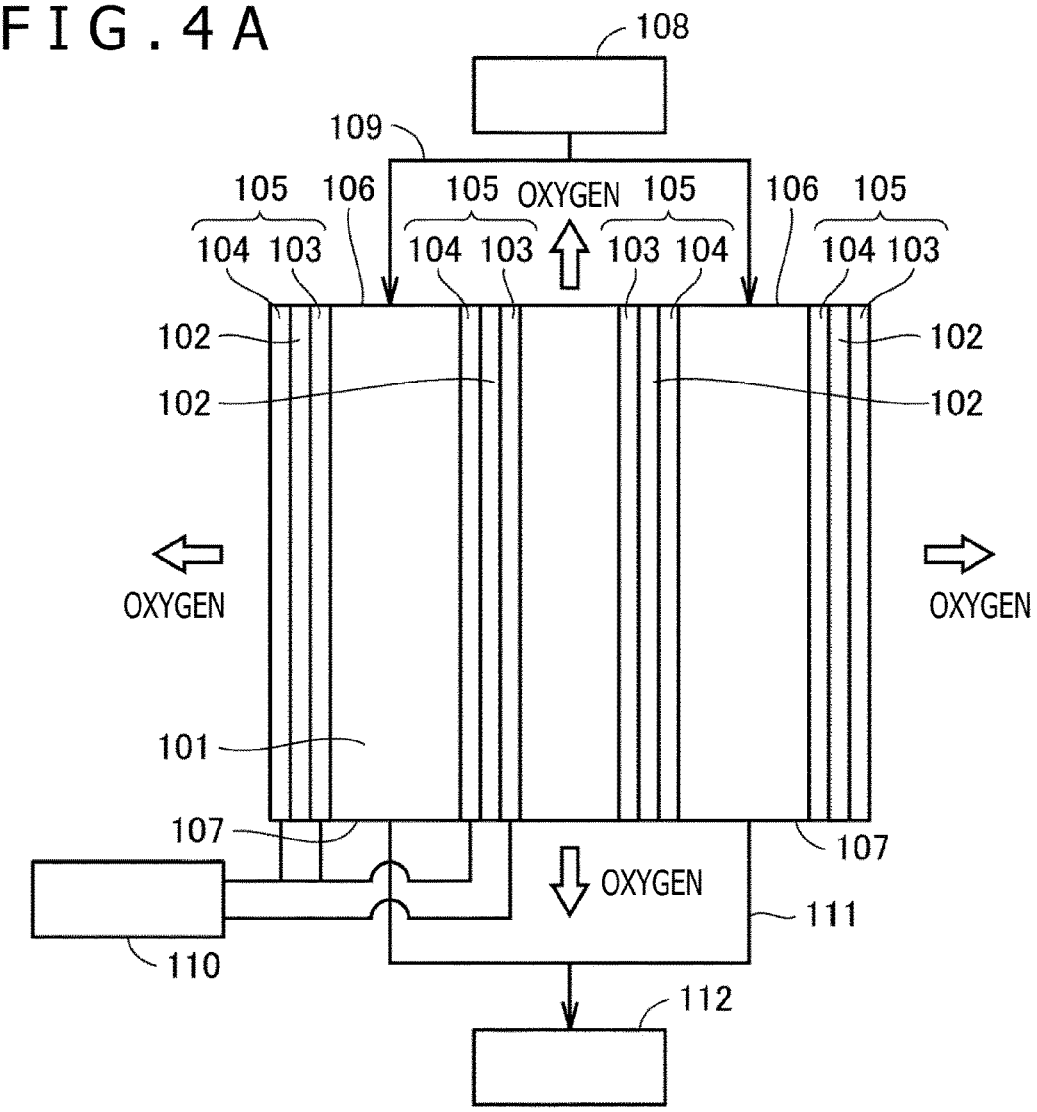
FIG. 4A is a schematic vertical cross-sectional view of a production system according to a fourth embodiment of the first mode of the present disclosure for methane.
Figure 4B:
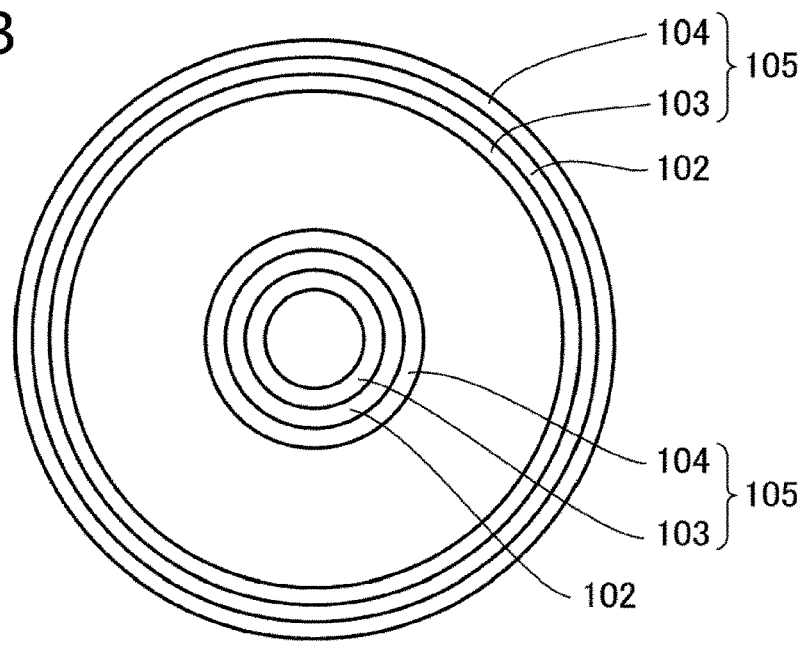
FIG. 4B is a schematic horizontal cross-sectional view of FIG. 4A.

FIGS. 4A and 4B illustrate a production system according to a fourth embodiment of the first mode of the present disclosure for methane (hereinafter called the "methane production system of the fourth embodiment"). FIG. 4A is a schematic vertical cross-sectional view of the methane production system of the fourth embodiment, and FIG. 4B is a schematic horizontal cross-sectional view of FIG. 4A. To elements illustrated in FIGS. 4A and 4B and designated by the same reference numerals as in FIG. 1, the above description is applicable. The methane production system illustrated in FIGS. 4A and 4B includes a cylindrical reaction vessel 101. The cylindrical reaction vessel 101 has an outer side wall formed by a first cylindrical solid electrolyte membrane 102 that includes cylindrical electrodes 103 and 104 on inner and outer surfaces thereof, respectively. In the cylindrical reaction vessel 101, a second cylindrical solid electrolyte membrane 102 is arranged with cylindrical electrodes 103 and 104 included on outer and inner surfaces thereof, respectively. The cylindrical reaction vessel 101 and the first and second cylindrical solid electrolyte membranes 102, 102 are coaxially arranged. Gas that is supplied from an inlet 106 and contains carbon dioxide and water comes into contact with both the electrodes 103, whereby electrolysis of water and production of methane take place. A methane-containing gas is then taken out from an outlet 107. Oxygen produced through the electrolysis of water is discharged out of the cylindrical reaction vessel 101 through the first and second, cylindrical solid electrolyte membranes 102. Owing to the inclusion of the first and second, electrode-including, cylindrical solid electrolyte membranes 102 on an inner side and outer side of the cylindrical reaction vessel 101, respectively, a greater area of contact is provided between the gas that contains carbon dioxide and water and the electrodes 103 and a hydrogenation catalyst included in the electrodes 103, and the gas hardly undergoes stagnation. The production of methane can hence be performed efficiently.

Production Method for Methane

Regarding a production method according to an embodiment of a second mode of the present disclosure for methane (hereinafter called the "methane production method of this embodiment"), a description will be made with reference to FIG. 5. FIG. 5 is a flow chart of the methane production method of this embodiment. The methane production method of this embodiment includes a gas supply step S10 of supplying gas that contains carbon dioxide and water, into a reaction vessel; a hydrogen production step S20 of producing hydrogen by subjecting water to electrolysis in the reaction vessel with use of a solid electrolyte membrane having an electrode group including at least a pair of electrodes, one of the electrodes functioning as a cathode side electrode, the other electrode functioning as an anode side electrode, the one electrode that functions as the cathode side electrode including a hydrogenation catalyst; a methane production step S30 of producing methane by reacting hydrogen and carbon dioxide in the presence of the hydrogenation catalyst, in the reaction vessel; and a gas discharge step S40 of discharging gas that contains methane, from the reaction vessel.

In the methane production method of this embodiment, all or any two or three of the above-described steps may be concurrently performed in combination, or the individual steps may be successively performed in the order of from step S10 to step S40. As a further alternative, any two or three of the steps may be concurrently performed in combination, and the remaining two steps or one step may be successively performed. Concurrent performance of the hydrogen production step S20 and the methane production step S30 is preferred from the viewpoint of facilitating efficient production of methane.

If desired to successively perform the gas supply step S10 to the gas discharge strep S40 in this order, these steps may be performed, for example, in the manner described below. After the gas that contains carbon dioxide and water is filled in the reaction vessel, the supply of the gas is stopped, the reaction vessel is brought into a hermetically sealed state, electrolysis of water is next performed in the reaction vessel to produce methane, and a methane-containing gas can then be discharged from the reaction vessel. Each step may successively be repeated twice or more either singly or in combination with one or more of the remaining steps.

In the gas supply step S10, the temperature of the gas that contains carbon dioxide and water and is to be supplied to the reaction vessel may be, but is not particularly limited to, for example, room temperature, or a temperature lower or higher than room temperature. If the temperature of the gas that contains carbon dioxide and water is relatively low, the solid electrolyte membrane can be heated from the viewpoint of facilitating the reaction between carbon dioxide and hydrogen in the methane production step S30.

As the gas that contains carbon dioxide and water, exhaust gas from an internal combustion engine such as an engine of a thermal power plant or automotive vehicle can be supplied, for example. Exhaust gas generally contains carbon dioxide and water, and is thus suitable for the methane production method of this embodiment.

To the reaction vessel, the above-described descriptions on the reaction vessels in the methane production systems of the first to fourth embodiments are applicable.

In the hydrogen production step S20, water is brought into contact with the electrode group to produce hydrogen through electrolysis. The water to be electrolyzed includes not only the water in the gas that contains carbon dioxide and water, but also water produced in the methane production step S30 to be described subsequently herein.

The solid electrolyte membrane that has the electrode group can be arranged inside the reaction vessel. Exposure of a portion or the entire portion of the solid electrolyte membrane to an outside of the reaction vessel can facilitate the discharge of oxygen that is produced through the electrolysis of water, to the outside of the reaction vessel. The electrode group includes at least a pair of electrodes. From the viewpoint of allowing the electrode group to function as an anode and a cathode in the electrolysis of water, the electrode group can be a pair of electrodes or a plurality of pairs of electrodes. Oxygen produced through the electrolysis of water can be discharged to the outside of the reaction vessel. The discharge of the oxygen to the outside of the reaction vessel can be facilitated by arranging the electrode that functions as an anode side electrode in the electrolysis of water, on an outer side wall of the reaction vessel.

Electric power to be supplied to the electrode group can be supplied, for example, by a thermoelectric generator or other generators. To the thermoelectric generator, the material for use in the thermoelectric generator, and the preferred temperature range of heat produced from the thermoelectric generator, the corresponding descriptions in the above-described methane production systems of the first to fourth embodiments are applicable.

The supplying of electric power from the thermoelectric generator to the electrode group is suited, because the electric power can be generated with heat produced in an internal combustion engine and exhaust gas produced from the internal combustion engine can be supplied as gas that contains carbon dioxide and water.

To the electrode group, the electrodes constituting the electrode group, the solid electrolyte membrane, and the internal combustion engine as well as the preferred material and thickness ranges of the electrode group, the electrodes, and the solid electrolyte membrane, the corresponding descriptions in the above-described methane production systems of the first to fourth embodiments are applicable.

In the methane production step S30, hydrogen and carbon dioxide are reacted in the presence of the hydrogenation catalyst in the reaction vessel, thereby producing methane.

To the hydrogenation catalyst and its preferred material range, the corresponding descriptions in the above-described methane production systems of the first to fourth embodiments are applicable. The hydrogenation catalyst may be included in the above-descried electrodes, or may form the above-descried electrodes.

Carbon dioxide and hydrogen may be reacted at a temperature of, for example, 300° C. and higher but 650° C. and lower, preferably 350° C. and higher but 600° C. and lower, more preferably 400° C. and higher but 550° C. and lower. The atmosphere in the reaction vessel can be heated to maintain the above-descried temperature range. The above-descried temperature range tends to facilitate the use of exhaust gas as gas that contains carbon dioxide and water.

In the gas discharge step S40, gas that contains the methane so produced can be discharged. The discharged gas can be supplied to a methane separator.

According to the methane production method of this embodiment, methane can be produced in an efficient manner and at low cost without contamination of the environment. The methane production method of this embodiment can be advantageously used in automotive vehicles, thermal power plants, and other equipment, in which internal combustion engines are included.

It should be understood by those skilled in the art that various modifications, combinations, sub-combinations and alterations may occur depending on design requirements and other factors insofar as they are within the scope of the appended claims or the equivalents thereof.

What is claimed is:

1. A production system for methane, comprising:
   a reaction vessel that includes:
      an inlet on a first side of the reaction vessel;
      an outlet on a second side of the reaction vessel different from the first side; and
      a wall including a solid electrolyte membrane and an electrode group that includes at least a pair of electrodes arranged on the solid electrolyte membrane, wherein
         a first electrode of the pair of electrodes functions as a cathode side electrode,
         a second electrode of the pair of electrodes functions as an anode side electrode, and
         the first electrode that functions as the cathode side electrode includes a hydrogenation catalyst.

2. The production system for methane according to claim 1, wherein the hydrogenation catalyst is platinum.

3. The production system for methane according to claim 1, wherein the solid electrolyte membrane includes yttria-stabilized zirconia.

4. The production system for methane according to claim 1, further comprising:
   an internal combustion engine.

5. The production system for methane according to claim 1, further comprising:
   a thermoelectric generator.

* * * * *